United States Patent [19]

Kitamura et al.

[11] 4,382,147

[45] May 3, 1983

[54] PROCESS FOR ISOLATING 4,4-DIHYDROXYDIPHENYL SULFONE FROM A MIXTURE OF DIHYDROXYDIPHENYLSULFONE ISOMERS

[75] Inventors: Hirotsugu Kitamura; Yasumasa Shimizu; Osami Ohura, all of Fuji, Japan

[73] Assignee: Tokai Denka Kogyo Kabushiki Kaisha, Japan

[21] Appl. No.: 300,502

[22] Filed: Sep. 9, 1981

[30] Foreign Application Priority Data

Oct. 31, 1980 [JP] Japan ................... 55-152228

[51] Int. Cl.$^3$ ............................................. C07C 147/10
[52] U.S. Cl. ..................................................... 568/33
[58] Field of Search ........................................... 568/33

[56] References Cited

U.S. PATENT DOCUMENTS

| 3,277,183 | 10/1966 | Heller et al. | 568/33 |
| 3,297,766 | 1/1967 | Bradley et al. | 568/33 |
| 4,162,270 | 7/1979 | Ogata et al. | 568/33 |

FOREIGN PATENT DOCUMENTS

| 38-5274 | 5/1963 | Japan | |
| 42-3005 | 2/1967 | Japan | |
| 43-24660 | 10/1968 | Japan | 568/33 |
| 47-43936 | 11/1972 | Japan | 568/33 |
| 50-106938 | 8/1975 | Japan | 568/33 |
| 51-52153 | 5/1976 | Japan | 568/33 |

OTHER PUBLICATIONS

J. Hinkel et al., J. Chem. Soc., pp. 2854–2856, (1949), 4:4'- and 2:4'-Dihydroxydiphenyl Sulfones.

Primary Examiner—Donald G. Daus
Assistant Examiner—M. C. Eakin
Attorney, Agent, or Firm—Scully, Scott, Murphy & Presser

[57] ABSTRACT 4,4'-Dihydroxydiphenyl sulfone is isolated from a mixture of dihydroxydiphenyl sulfone isomers by heat dissolving the mixture in phenol and then cooling the resulting solution thereby allowing 4,4'-dihydroxydiphenyl sulfone to precipitate as an adduct with phenol.

5 Claims, No Drawings

PROCESS FOR ISOLATING 4,4-DIHYDROXYDIPHENYL SULFONE FROM A MIXTURE OF DIHYDROXYDIPHENYLSULFONE ISOMERS

BACKGROUND OF THE INVENTION

This invention relates to an isolation process for a dihydroxydiphenyl sulfone isomer. More particularly, it is concerned with a process for isolating a high purity 4,4'-dihydroxydiphenyl sulfone from an isomer mixture consisting of 4,4-dihydroxydiphenyl sulfone and 2,4'-dihydroxydiphenyl sulfone.

4,4'-Dihydroxydiphenyl sulfone, due to the uniqueness of its diphenyl sulfone linkage, has a heat resistance, a resistance to oxidation and a stability to light, and because of these characteristics 4,4'-dihydroxydiphenyl sulfone has a recent tendency to its increasing utilization as a substitute for bisphenol A in the field of plastics such as polyester resins, epoxy resins and polycarbonate resins.

In general, as a process for preparing 4,4'-dihydroxydiphenyl sulfone there are known a process wherein phenol and a sulfonating agent such as a concentrated sulfuric acid, a fuming sulfuric acid or a sulfuric anhydride are reacted with each other, and a process wherein phenol and p-phenolsulfonic acid are reacted with each other. According to those manufacturing processes, however, not only it is impossible to avoid the formation as a side reaction product of 2,4'-dihydroxydiphenyl sulfone, an isomer of 4,4'-dihydroxyphenyl sulfone, but also it is not easy to isolate 4,4'-dihydroxydiphenyl sulfone from this isomer mixture, therefore, a fairly large amount of 2,4'-isomer is contained in ordinary industrial products.

As previously noted, 4,4'-dihydroxydiphenyl sulfone is a compound which is not having many application aspects in the field of high polymer industry as a substitute for bisphenol A. In this case, a high polymer prepared from 4,4'-dihydroxydiphenyl sulfone containing 2,4'-isomer is small in molecular weight and exhibits deterioration in mechanical properties as compared with one prepared from 4,4'-dihydroxyphenyl sulfone not containing 2,4'-isomer, and the larger the content of 2,4'-isomer the more noticeable becomes this tendency. For effective industrial utilization of 4,4'-dihydroxydiphenyl sulfone, therefore, it is necessary to remove the coexistent 2,4'-dihydroxydiphenyl sulfone and isolate 4,4'-dihydroxydiphenyl sulfone in high purity.

Heretofore, as a purification process for 4,4'-dihydroxydiphenyl sulfone there have been known recrystallization from water, recrystallization from an aqueous methanol solution, or washing with a hot aqueous solution at above 120° C. containing an aliphatic higher alcohol (see Japanese Patent Publication No. 3005/67). However, these processes are effective for removing colored impurity and resinous substance contained in a crude dihydroxydiphenyl sulfone mixture and are not effective for removing the 2,4'-dihydroxydiphenyl sulfone isomer. Therefore, as a process for separating 2,4'-dihydroxydiphenyl sulfone, there have been proposed a separation process based on the formation of a calcium complex (see U.S. Pat. No. 2,392,137) and a separation process based on the formation of a benzene adduct [see "Journal of Chemical Society" (1949), pp. 2854–2856], but these processes are industrially unsuitable because they require complicated operations.

As an industrial process for the separation of 2,4'-dihydroxydiphenyl sulfone there have been proposed a process using sym-tetrachloroethane as an extraction solvent (see Japanese Patent Publication No. 5274/63), a process using o-dichlorobenzene as an extraction solvent (see Japanese Patent Publication No. 24660/68) and a process using mono-, di- and trialkylphenol as extraction solvents (see Japanese Patent Publication No. 43936/72). However, the solubility of 2,4'-dihydroxydiphenyl sulfone in those solvents at ordinary temperature is so low that it is difficult to fully separate 2,4'-dihydroxydiphenyl sulfone from the isomer mixture at ordinary temperature. In view of this point, all of the aforesaid three processes adopt a high temperature treatment (100°–150° C.) such as a hot filtration for increasing the solubility of 2,4'-dihydroxydiphenyl sulfone in those solvents thereby improving the effect of its separation from the isomer mixture. In such a high temperature treatment, however, drawbacks are unavoidable, such as the complexity of operation, damage of filter materials, etc., contamination of the working environment caused by solvent vaporization and the resulting hygienic problems. Thus, those processes are not considered to be fully satisfactory processes industrially.

SUMMARY OF THE INVENTION

It is an object of this invention to eliminate the foregoing drawbacks associated with the conventional processes.

It is another object of this invention to provide a process for isolating a high purity 4,4'-dihydroxydiphenyl sulfone in a simple manner from a mixture of 4,4'-dihydroxydiphenyl sulfone and 2,4'-dihydroxydiphenyl sulfone.

Other objects and advantages of this invention will become apparent from the following description.

The above-mentioned objects of this invention can be attained by heat dissolving in phenol an isomer mixture of 4,4'-dihydroxydiphenyl sulfone and 2,4'-dihydroxydiphenyl sulfone and then cooling the resulting solution thereby allowing 4,4'-dihydroxydiphenyl sulfone to precipitate as an adduct with phenol.

DETAILED DESCRIPTION OF THE INVENTION

The isomer mixture used in the process of this invention consists of any proportions of 4,4'-dihydroxydiphenyl sulfone and 2,4'-dihydroxydiphenyl sulfone, but usually an isomer mixture consisting of more than 70% by weight of 4,4'-dihydroxydiphenyl sulfone and less than 30% by weight of 2,4'-dihydroxydiphenyl sulfone is preferably used in the isolation operation according to the present invention.

The dissolving of the isomer mixture in phenol is performed under heating at a temperature usually above about 60° C. There is no special limit to the upper limit of the heating temperature, but even heating at a temperature higher than 100° C. would not bring about any particular effect. Usually, heating temperatures below 100° C. are satisfactory.

The cooling temperature is usually below about 50° C. and it should be a temperature at which the phenol solvent itself does not crystallize.

In working the process of this invention, the dissolving of the isomer mixture in phenol and the isolation may be carried out under any of the following conditions—reduced pressure, normal pressure and pressurized condition—, but usually are conducted under normal pressure.

After dissolving the entire isomer mixture in phenol, the resulting solution is cooled whereby only 4,4'-dihydroxydiphenyl sulfone crystallizes as an adduct of phenol. Then, liquid components such as the solvent are separated from this system by any suitable means, e.g. filtration by suction, pressure filtration and centrifugal separation.

When separating from the solvent system the crystals of the 4,4'-dihydroxydiphenyl sulfone/phenol adduct precipitated from the phenol solvent, if the temperature of the solution is cooled to lower than 41° C. which temperature corresponds to the melting point of phenol, the solution itself will solidify with the result that the crystals formed are no longer separable; therefore, it is desirable that the solution be held at a temperature of 41° C. or higher. If it is industrially disadvantageous to maintain the solution temperature at such a level, it is preferable that water be added into the system, whereby the solution can be prevented from solidifying even at ordinary temperature. The amount of water to be added is preferably less than 20% by weight based on the amount of phenol.

There is no special limit to the amount of phenol for isolating a high purity 4,4'-dihydroxydiphenyl sulfone from the mixture of dihydroxydiphenyl sulfone isomers if only it corresponds to an amount capable of completely dissolving the entirety of 2,4'-dihydroxydiphenyl sulfone contained in the isomer mixture and an amount capable of completely heat dissolving the entirety of the isomer mixture. Preferably, the amount of phenol is such an amount that the crystals of 4,4'-dihydroxydiphenyl sulfone/phenol adduct precipitated by cooling after heat dissolution form a slurry in the solution with a slurry concentration of less than 30% by weight.

If the concentration as a slurry of the crystals formed exceeds 30% by weight, it becomes difficult to separate the crystals, and consequently it is possible that there will be formed phenol adduct crystals of 4,4'-dihydroxydiphenyl sulfone containing a larger amount of 2,4'-dihydroxydiphenyl sulfone.

The process of this invention is applicable to 4,4'-dihydroxydiphenyl sulfone crystals containing 2,4'-isomer. In the process of the invention, moreover, phenol may be added directly to the product obtained by a dihydroxydiphenyl sulfone preparing reaction; that is, the process of this invention may be practised in such a manner that phenol is added directly to the reaction system containing dihydroxydiphenyl sulfone resulting from the reaction of phenol with a sulfonating agent such as a concentrated sulfuric acid, a fuming sulfuric acid or a sulfuric anhydride or with p-phenolsulfonic acid.

From the high purity 4,4'-dihydroxydiphenyl sulfone obtained according to the process of this invention there can be removed phenol easily by heating the adduct as it is or in an aqueous solution, whereby there can be obtained crystals of a high purity 4,4'-dihydroxydiphenyl sulfone.

According to the process of this invention, not only a high purity 4,4'-dihydroxydiphenyl sulfone can be isolated as an adduct with phenol extremely effectively from a mixture of dihydroxydiphenyl sulfone isomers by utilization of the relatively cheap and industrially fully utilizable phenol as a solvent, but also the phenol which has been used in the isolation and purification is employable as it is as a reaction material of dihydroxydiphenyl sulfone. The process of this invention has a further advantage that the isolation and purification operation is very easy without requiring any special means such as hot filtration required in the prior art processes; besides, the problems caused by the isolation operation at a high temperature performed in the prior art processes, such as the damage of filter materials, etc. and problems related to environmental sanitation, are not likely to occur at all. Thus, the process of this invention is an extremely advantageous process industrially.

Working examples of this invention will be given hereinunder for further illustration of the invention, but it is to be understood that the invention is not limited thereto.

EXAMPLE 1

A dihydroxydiphenyl sulfone isomer mixture consisting of 20 g, 2,4'-dihydroxydiphenyl sulfone and 80 g. 4,4'-dihydroxydiphenyl sulfone was added with stirring into 200 g. of phenol heated at 80° C. After dissolving completely, the solution was cooled to 45° C. to crystallize a 4,4'-dihydroxydiphenyl sulfone/phenol adduct. While maintaining the solution at a temperature of 45° C., the crystals thus formed were separated by suction filtration to yield 43.2 g. of the crystals, which were then dried at 140° C. under a reduced pressure of 30 mmHg to give 28.9 g. of dried crystals. The purity of 4,4'-dihydroxydiphenyl sulfone in the dried crystals was 99.2%.

EXAMPLE 2

A dihydroxydiphenyl sulfone isomer mixture consisting of 20 g. 2,4'-dihydroxydiphenyl sulfone and 80 g. 4,4'-dihydroxydiphenyl sulfone was added into 200 g. of a phenol solution containing 10% water, followed by heating to 90° C. with stirring. After dissolving the isomer mixture completely, the solution was cooled to 20° C. to crystallize a 4,4'-dihydroxydiphenyl sulfone/phenol adduct, which was then separated by centrifugal separation to give 81.4 g. of crystals.

The crystals were put into 1 liter of water and heated to 100° C. with stirring to allow the phenol contained therein to be extracted into the water layer. Then, after cooling to 20° C., the crystals were separated and dried to obtain 58.9 g. of product, which product contained 99.4% of 4,4'-dihydroxydiphenyl sulfone.

EXAMPLE 3

250 g. of phenol was heated to 170°–180° C. with stirring together with 100 g. of 98% sulfuric acid, and the distilled azeotropic mixture was cooled and separated into two layers, and the lower phenol layer was continuously returned to the reaction vessel while reaction was allowed to proceed for 3 hours.

After the reaction, 250 g. of a phenol solution containing 10% of water was added into the reaction system containing a dihydroxydiphenyl sulfone mixture as the reaction product while maintaining the reaction system at 80° C. The reaction system was finally cooled to 20° C. thereby allowing a 4,4'-dihydroxydiphenyl sulfone adduct to crystallize, which adduct was then separated in a centrifugal separator to give 141.7 g. of crystals. The crystals were put into 2 liters of water and heated to 80° C. with stirring to allow the phenol contained therein to be extracted into the water layer. Then, after cooling to 20° C., the crystals were separated and dried to obtain 96.2 g. of product, which contained 99.5% of 4,4'-dihydroxydiphenyl sulfone.

What is claimed is:

1. A process for isolating 4,4'-dihydroxydiphenyl sulfone from a mixture of dihydroxydiphenyl sulfone isomers, which process consists essentially of heat dissolving in phenol and water an isomer mixture consisting of 4,4'-dihydroxydiphenyl sulfone and 2,4'-dihydroxydiphenyl sulfone and then cooling the resulting solution thereby allowing 4,4'-dihydroxydiphenyl sulfone to precipitate as an adduct with phenol wherein the water is present in an amount less than 20% by weight based on the amount of phenol, the dissolving of said isomer mixture is performed at about 60° C. to about 100° C., and the cooling of the resulting solution is performed at a temperature lower than about 50° C.

2. A process according to claim 1, in which said isomer mixture consists of more than 70% by weight of 4,4'-dihydroxydiphenyl sulfone and less than 30% by weight of 2,4'-dihydroxydiphenyl sulfone.

3. A process according to claim 1, in which the amount of phenol is such an amount that the crystals of the 4,4'-dihydroxydiphenyl sulfone/phenol adduct precipitated form a slurry in the solution with a slurry concentration of less than 30% by weight.

4. A process according to claim 1, in which the precipitated 4,4'-dihydroxydiphenyl sulfone/phenol adduct is heated as it is or in an aqueous solution thereby removing phenol.

5. A process according to claim 1, in which said isomer mixture is a product obtained by a dihydroxydiphenyl sulfone preparing reaction.

* * * * *